United States Patent
Karinka et al.

(10) Patent No.: US 6,939,450 B2
(45) Date of Patent: Sep. 6, 2005

(54) DEVICE HAVING A FLOW CHANNEL

(75) Inventors: Shridhara Alva Karinka, Lowell, MA (US); Mark E. Tess, Merrimack, NH (US)

(73) Assignee: Abbott Laboratories, Abbott Park, IL (US)

( * ) Notice: Subject to any disclaimer, the term of this patent is extended or adjusted under 35 U.S.C. 154(b) by 65 days.

(21) Appl. No.: 10/266,548

(22) Filed: Oct. 8, 2002

(65) Prior Publication Data

US 2004/0067166 A1 Apr. 8, 2004

(51) Int. Cl.$^7$ ................... G01N 27/327; G01N 21/00; B01L 3/00; B01L 3/02
(52) U.S. Cl. ............ 204/409; 204/403.01; 204/403.14; 204/409; 422/58; 422/99
(58) Field of Search ............... 422/55–58, 82.01–82.03, 422/100, 99; 204/409, 403.01, 403.14, 403.03

(56) References Cited

U.S. PATENT DOCUMENTS

| | | | |
|---|---|---|---|
| 3,617,362 A | * 11/1971 | Bemmels et al. | 428/355 R |
| 4,111,769 A | * 9/1978 | Stueben | 522/139 |
| 4,426,451 A | * 1/1984 | Columbus | 436/518 |
| 4,437,999 A | 3/1984 | Mayne | 210/748 |
| 4,849,340 A | 7/1989 | Oberhardt | 422/110 |
| 5,141,868 A | 8/1992 | Shanks et al. | 435/287.9 |
| 5,405,510 A | * 4/1995 | Betts et al. | 205/782 |
| 5,509,410 A | 4/1996 | Hill et al. | 600/39.3 |
| 5,582,697 A | * 12/1996 | Ikeda et al. | 205/777.5 |
| 5,628,890 A | 5/1997 | Carter et al. | 204/403.05 |
| 5,759,364 A | 6/1998 | Charlton et al. | 204/403.14 |
| 5,997,817 A | 12/1999 | Crismore et al. | 204/403.1 |
| 6,207,000 B1 | 3/2001 | Schwobel et al. | 156/248 |
| 6,540,962 B1 | * 4/2003 | Okubo et al. | 422/58 |
| 6,581,899 B2 | * 6/2003 | Williams | 251/7 |
| 6,645,359 B1 | * 11/2003 | Bhullar et al. | 204/403.01 |
| 2002/0003001 A1 | 1/2002 | Weigl et al. | 137/806 |
| 2002/0036018 A1 | 3/2002 | McNeely et al. | 137/809 |

FOREIGN PATENT DOCUMENTS

| | | | | |
|---|---|---|---|---|
| EP | 0261531 A1 | * 3/1988 | | G01N/21/07 |
| EP | 0 359 831 | 3/1990 | | |
| EP | 1 074 832 | 2/2001 | | |
| EP | 1 167 538 | 1/2002 | | |
| EP | 1 195 441 | 4/2002 | | |
| JP | 01-134242 A | * 5/1989 | | G01N/27/30 |
| WO | WO 99/58245 A1 | * 11/1999 | | B01L/3/00 |
| WO | 01/25138 | 4/2001 | | |
| WO | 0173124 | 10/2001 | | |
| WO | 01/73395 | 10/2001 | | |

OTHER PUBLICATIONS

Pages 93–96 of vol. 9 of the 4$^{th}$ edition of the Kirk–othmer Encyclopedia of Chemical Technology John Wiley & Sons 1994.*

JPO abstract of 01–134242 A (Kawaguri et al.).*

Pressure—Sensitive Adhesives and Products, Encyclopedia of Polymer Science and Engineering, vol. 13, John Wiley & Sons, 1988, pp. 345–368.

* cited by examiner

*Primary Examiner*—Alex Noguerola
(74) *Attorney, Agent, or Firm*—David L. Weinstein

(57) ABSTRACT

A device having a flow channel, wherein at least one flow-terminating interface is used to control the flow of liquid in the flow channel. The flow-terminating interface prevents the flow of the liquid beyond the interface. In one aspect, the invention provides a sensor, such as, for example, a biosensor, in the form of a strip, the sensor being suitable for electrochemical or optical measurement. The sensor comprises a base layer and a cover layer, and the base layer is separated from the cover layer by a spacer layer. The base layer, cover layer, and spacer layer define a flow channel into which a liquid sample is drawn therein and flows therethrough by means of capillary attraction. The flow of the sample is terminated by a flow-terminating interface positioned in the flow channel.

23 Claims, 4 Drawing Sheets

DEVICE HAVING A FLOW CHANNEL

FIELD OF THE INVENTION

This invention relates to a device for controlling the flow of a fluid in a channel where the flow results from capillary attraction. More particularly, the invention relates to a sensor for controlling the taking up of a liquid sample into the reaction site of the sensor.

DISCUSSION OF THE ART

Controlling the flow of fluid in a channel where the flow results from capillary attraction is important in microfluidic and microanalytical systems. The volume of fluid in an area where a chemical reaction is to be carried out often is required to be controlled to ensure precise control of the reaction or precise quantification of the analyte of interest or both.

The control of the flow of a fluid may be required in order to complete a reaction step before another reaction step commences. The control of the flow of fluid may also be required to control the effects of dilution. The control of the flow of fluid may also be required to maintain the flow after the completion of the reaction.

The prior art discloses numerous electrochemical and optical test strips for measuring the concentration of analyte in a test sample. In particular, the art discloses disposable test strips for the measurement of glucose level in whole blood that deal primarily with the reaction layer used to generate an analytical response, the mode of measurement, and the algorithms used in the measurement.

Introduction of a liquid sample to these test strips can be achieved in several ways. A simple approach is to place a sample of liquid directly onto the reaction site. A second approach is to define a cavity having dimensions small enough to allow the liquid sample to be taken up by capillary attraction. An alternative to the use of capillary attraction is to place a mesh in the sample path to aid in transporting the sample by wicking action to fill the reaction site.

U.S. Pat. No. 5,509,410 discloses a strip comprising an elongated support (preferably flat) adapted for releasable attachment to readout circuitry; a first conductor and a second conductor each extending along the support and comprising means for connection to the circuitry. An active electrode, positioned to contact a liquid mixture and the first conductor, comprises a deposit of enzyme capable of catalyzing a reaction involving a compound and (preferably) an electron mediator, capable of transferring electrons between the enzyme-catalyzed reaction and the first conductor. A reference electrode is positioned to contact the mixture and the second conductor.

U.S. Pat. No. 5,141,868 discloses a specifically-reactive sample-collecting and testing device having a cavity or cavities, the dimensions of which are small enough to enable a liquid sample to be drawn into the cavity or cavities by capillary attraction. The cavity includes an electrode arrangement for measuring one or more electrical characteristics of the sample. A surface of a wall of the cavity optionally bears a coating of a material that is appropriate for the test to be carried out in the device. In the device, the sample flows by capillary attraction into a biosensor to a point defined by the interface of the cover layer and air. A drawback of this device is that the cavity is filled until the aperture created by the discontinuity of the bonding and the plate is encountered. Errors in the measurement of the concentration of an analyte in a sample of fluid occur if the dimensions of the cavity are such that the assay begins prior to the sample's reaching a state of quiescence.

U.S. Pat. Nos. 5,759,364; 5,437,999; 5,997,817; and 6,207,000 describe aspects of the use of flow channels that employ capillary attraction for transporting biological samples in electrochemical test strips.

U.S. Pat. No. 5,628,890 discloses a sensor that utilizes a mesh layer placed between the surface of the substrate and the cover layer to reduce the surface tension of the sample so that the sample flows into the flow channel by means of chemical wicking. The flow channel is defined by printing a hydrophobic insulating layer through the mesh. Applying the mesh layer is a time-consuming step, and a biosensor employing a mesh layer may require a larger sample than does a biosensor not employing a mesh layer, primarily because a flow channel having greater dimensions may be required to insert a layer of mesh. Removal of the mesh layer would result in saving time, reducing cost, and reducing the volume of sample required.

SUMMARY OF THE INVENTION

The present invention provides a device having a flow channel, wherein at least one flow-terminating interface is used to control the flow of liquid in the flow channel. The flow-terminating interface prevents the flow of the liquid beyond the interface.

In one aspect, the invention provides a sensor, such as, for example, a biosensor, in the form of a strip, the sensor being suitable for electrochemical or optical measurement. The sensor comprises a base layer and a cover layer, and the base layer is separated from the cover layer by a spacer layer. The base layer, cover layer, and spacer layer define a flow channel into which a liquid sample is drawn into and flows through by means of capillary attraction. The flow of the sample is terminated by a flow-terminating interface positioned in the flow channel.

In a preferred embodiment, the sensor is in the form of a strip and comprises:

(a) a base layer having a first major surface and a second major surface;

(b) a cover layer having a first major surface and a second major surface, the first major surface of the cover layer facing the first major surface of the base layer;

(c) a spacer layer interposed between the first major surface of the cover layer and the first major surface of the base layer to separate the cover layer from the base layer;

(d) a flow channel having walls formed by the first major surface of the cover layer, the first major surface of the base layer, and the spacer layer, the flow channel having a reaction site, the flow channel being of such dimensions that a liquid sample can be drawn therein and can flow therethrough by means of capillary attraction;

(e) a flow-terminating interface applied to or formed in the first major surface of the cover layer, the interface capable of terminating flow of a liquid sample in the flow channel;

(f) a sample application zone, where the liquid sample is introduced into the flow channel; and (g) at least one opening communicating with the flow channel to allow gas to be vented from the flow channel.

The reaction site can include an electrode arrangement or an optical arrangement. An electrode arrangement comprises at least a working electrode and a reference electrode in the flow channel. In conjunction with the electrode arrangement, at least one reagent for a specified assay can be located at or transported to the reaction site. An optical arrangement requires that at least a portion of the flow channel comprises a light transmissive material so that a source of light can transmit light through the light transmissive material to provide a signal related to the presence or the amount of an analyte in the sample, e.g., absorbance or reflectance, which signal can be detected and measured. In conjunction with the light transmissive material, at least one reagent for a specified assay can be located at or transported to the reaction site.

In a preferred embodiment, the spacer layer defines the sidewalls of the flow channel, while the cover layer forms the top wall of the flow channel and the base layer forms the bottom wall of the flow channel. In order to terminate the flow of the sample in the flow channel, a flow-terminating interface is established in or on the cover layer at a specified distance from the sample application zone. Air can be vented from the flow channel via at least one opening formed in the spacer layer, in the cover layer, or in the base layer, the at least one opening communicating with the flow channel.

The flow-terminating interface can operate by one or more physical mechanisms. For example, a physical mechanism that has been found to be useful involves employing a hydrophilic/hydrophobic interface, wherein a hydrophilic fluid flows along a hydrophilic surface until the flowing fluid encounters a hydrophobic barrier in the flow channel; alternatively, a hydrophobic fluid flows along a hydrophobic surface until the flowing fluid encounters a hydrophilic barrier in the flow channel. Another physical mechanism that has been found to be useful involves a barrier that disrupts the capillary attraction of the fluid for the surface along which it is flowing. Still another physical mechanism that has been found to be useful involves a change in the dimensions of the flow channel that disrupts the capillary attraction of the fluid for the surface along which it is flowing.

In the case of a sensor employing a hydrophilic/hydrophobic interface for a sample comprising a hydrophilic liquid, the first major surface of the cover layer is hydrophilic. The hydrophilic/hydrophobic interface can be formed on the cover layer by applying a layer of hydrophobic material over a portion of the cover layer to generate a hydrophilic/hydrophobic interface. The sample of hydrophilic liquid flows along the hydrophilic surface of the cover layer until the hydrophilic/hydrophobic interface is reached. In an alternative embodiment, the cover layer can be a layer of hydrophobic material having a hydrophilic coating on at least a portion of the first major surface thereof. A portion of the hydrophilic coating that has been applied to the hydrophobic cover layer can be removed by mechanical scraping or ablating (such as, for example, by means of a laser) to form the hydrophilic/hydrophobic interface by exposing the hydrophobic material of the cover layer.

While the invention is contemplated primarily for hydrophilic liquids, the flow channel can be modified to accommodate samples of hydrophobic liquids. In the event that the sample is a hydrophobic liquid, a cover layer in which the first major surface is hydrophobic can be used. A layer of hydrophilic material can be applied to a portion of the hydrophobic surface to generate a hydrophilic/hydrophobic interface. The sample of hydrophobic liquid flows along the hydrophobic surface of the cover layer until the hydrophilic/hydrophobic interface is reached. In an alternative embodiment, the cover layer can be a layer of hydrophilic material having a hydrophobic coating on at least a portion of the first major surface thereof. A portion of the hydrophobic coating that has been applied to the hydrophilic cover layer can then be removed, either by mechanical scraping or ablating, to form the hydrophilic/hydrophobic interface by exposing the hydrophilic material of the cover layer.

In the case of either a hydrophilic liquid flowing along a hydrophilic surface or a hydrophobic liquid flowing along a hydrophobic surface, a flow-terminating interface can be introduced in the first major surface of the cover layer along which the liquid is flowing by capillary attraction by forming a plurality of openings in the cover layer, which openings are of sufficient size and are located at sufficiently close intervals such that the capillary attraction is disrupted, whereby the force that allows the liquid to flow in the flow channel is resisted. This effect can also be brought about by increasing the dimensions of the flow channel at a desired location, wherein that the capillary attraction is disrupted, whereby the force that allows the liquid to flow in the flow channel is resisted.

In accordance with this invention, the flow channel is designed so that liquid samples flow along those major surfaces or portions of major surfaces of the flow channel that contain the flow-terminating interface. The flow channel is designed so that liquid samples do not flow along those major surfaces or portions of those major surfaces of the flow channel that do not contain a flow-terminating interface. This design is necessary so that the liquid sample will cease to flow when it encounters the flow-terminating interface.

The air in the flow channel can be vented from at least one opening in the sidewalls of the flow channel. In an alternate embodiment, the flow channel is closed at the distal end and has no openings in the sidewalls. In this embodiment, the sensor strip can be vented through the cover layer by at least one, and preferably a plurality of, openings formed therein. The use of a plurality of openings in the cover layer eliminates the problem that results from the use of a single opening that is improperly positioned with respect to the flow channel, with the result that the opening does not connect the flow channel with the external environment. If two or more openings are employed, and if these openings are separated from one another, there is a higher probability that at least one of the openings will serve to vent air from the flow channel. The openings are preferably placed sufficiently close to each other so that no matter how the cover layer is placed over the flow channel, at least one opening, and preferably more than one opening, is positioned over the flow channel to allow venting. At the same time, the openings are preferably separated by sufficient distance so that the mechanical strength of the cover layer is not diminished. Furthermore, these openings can perform the additional function of acting as a flow-terminating interface, so that liquid does not flow beyond these openings. These openings should be separated from one another by appropriate distances, such that the capillary attraction between the sample and the first major surface of the cover layer is disrupted, whereby the sample does not flow beyond the openings.

In the sensor strip of this invention, the flow-terminating interface prevents the sample from flowing beyond a specified location, whereby the volume of sample required is reduced. The sample is introduced to the sensor strip at the sample application zone, and the sample traverses the flow channel by means of the force resulting from capillary attraction. The sample flows along the flow channel until the flow-terminating interface is reached. At the flow-terminating interface, the force resulting from capillary attraction is not sufficient to overcome the obstacle generated by the flow-terminating interface. More than one flow-terminating interface can be used in systems where the sample may be required to flow to different branches of the flow channel, such as, for example, in a microfluidic system. Additional flow-terminating interfaces also can be used to ensure that perturbation of the sample does not force the sample to flow beyond the desired point of termination of the flow of the sample.

DETAILED DESCRIPTION

As used herein, the expression "capillary attraction" means the force that results from greater adhesion of a liquid to a solid surface than internal cohesion of the liquid itself and causes the liquid to flow along a surface, as water is in a clean glass tube. The expression "reaction site" means that portion of the sensor that contains materials related to the reaction that must take place in order to carry out an assay. The reaction site for an electrochemical sensor includes an arrangement comprising at least a reference electrode and a working electrode. The reaction site of a photometric sensor includes an arrangement comprising an area at which light is transmitted into the flow channel, whereby a change in a property of the light so transmitted is detected. If the sensor includes an optional reagent, the reagent interacts with the sample and assists in the assay by undergoing a change related to the test, whereby a measurement based on a reaction involving the reagent is carried out in conjunction with the electrode arrangement or the photometric arrangement, whichever arrangement is employed. The term "hydrophilic" means a characteristic of a surface having an affinity for an aqueous fluid or a characteristic of a surface that is capable of being smoothly wetted by an aqueous fluid. The term "hydrophobic" means a characteristic of a surface not having an affinity for an aqueous fluid or a characteristic of a surface that is not capable of being smoothly wetted by an aqueous fluid.

Figure 1:
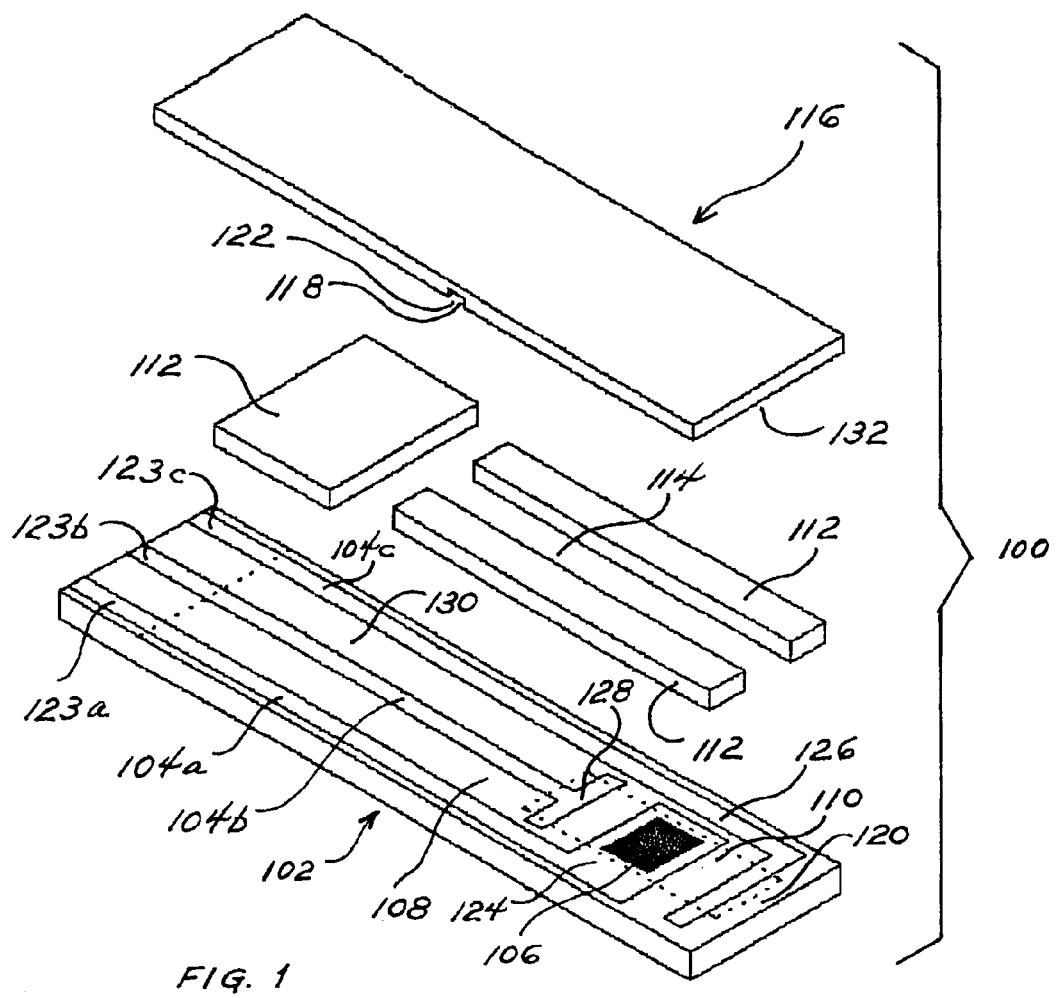
FIG. 1 is an exploded perspective view of one embodiment of the sensor strip of this invention.
Figure 2:
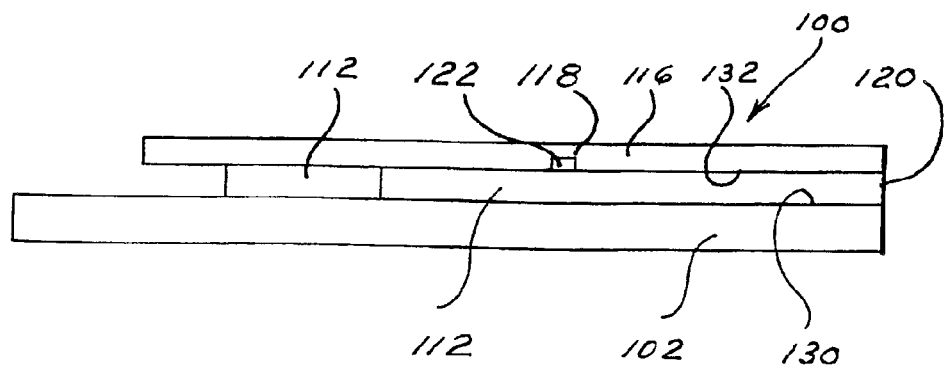
FIG. 2 is a side view in elevation of the sensor strip shown in FIG. 1.
Figure 3:
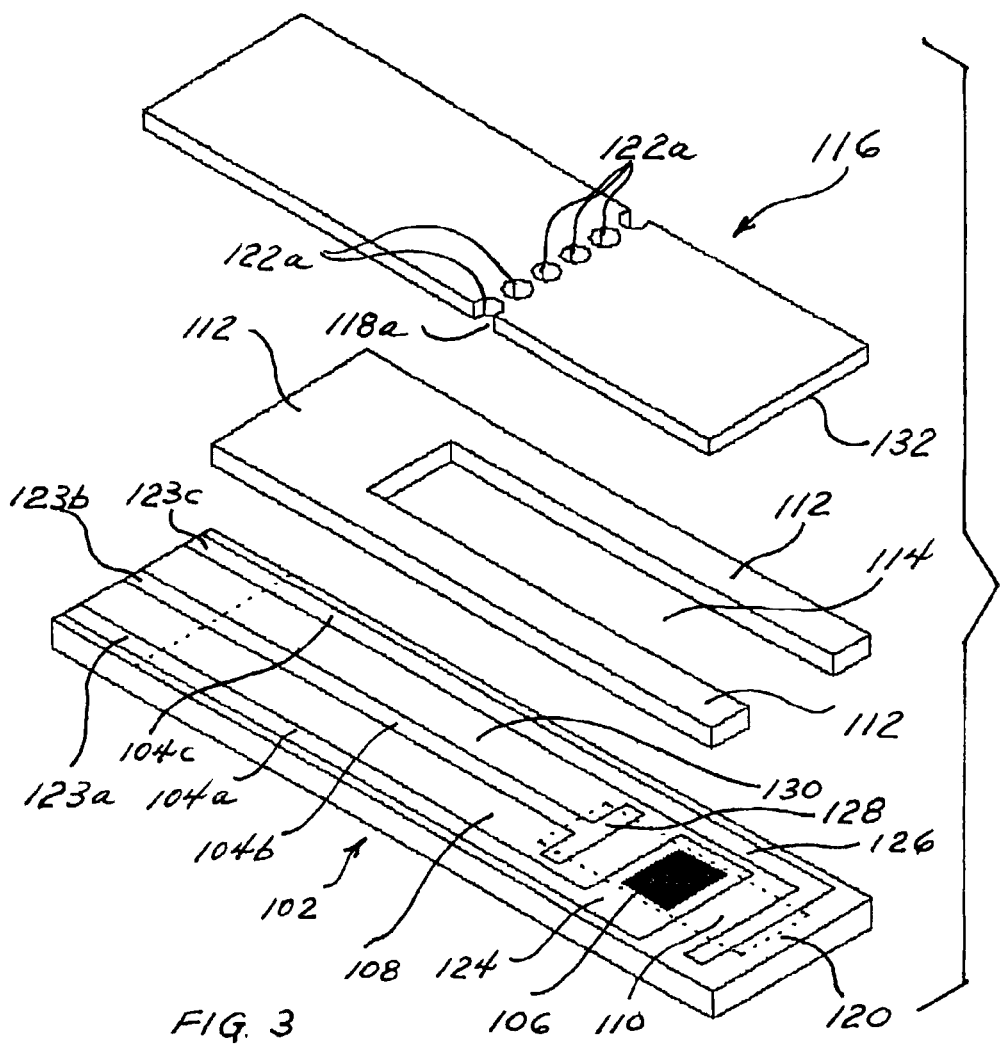
FIG. 3 is an exploded perspective view of another embodiment of the sensor strip of this invention.
Figure 4:
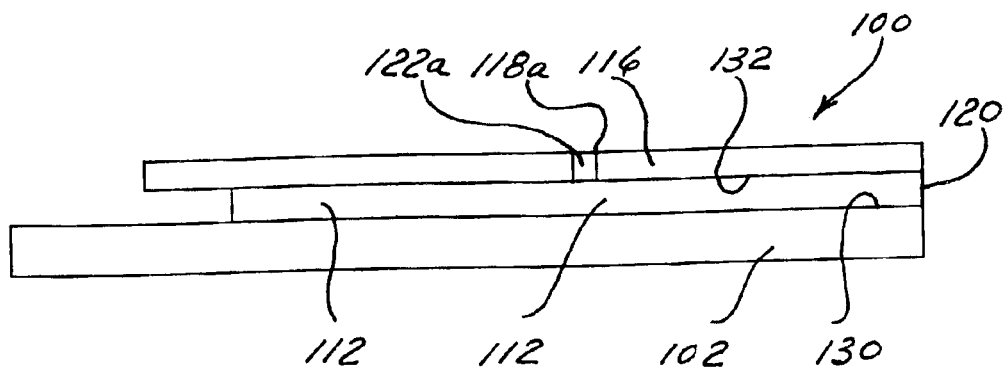
FIG. 4 is a side view in elevation of the sensor strip shown in FIG. 3.

FIGS. 1 and 2 illustrate one embodiment of a sensor strip in accordance with this invention. FIGS. 3 and 4 illustrate another embodiment of a sensor strip made in accordance with this invention. In order to simplify the discussion of these embodiments, those parts having the same function in each embodiment will have the same reference numeral. The embodiments differ primarily in the nature of the flow-terminating interface and in the nature of the openings forming the vents. Those parts in FIGS. 3 and 4 that are substantially different from those parts in FIGS. 1 and 2 will be distinguished by the suffix "a". Accordingly, in FIGS. 3 and 4, the reference numerals for the flow-terminating interface and the openings for the vents will be followed by the suffix "a".

Referring now to FIGS. 1, 2, 3, and 4, a sensor strip 100 comprises a base layer 102, conductive tracks 104a, 104b, and 104c for electrochemical use, a reaction site 106, an insulation layer 108 to delineate a specified sensor area 110, a spacer layer 112 to specify the width and depth of a flow channel 114, a cover layer 116 to enclose the flow channel 114. The sample is caused to flow in the flow channel 114 by means of capillary attraction.

The cover layer 116 includes a flow-terminating interface for terminating the flow of the sample. In FIGS. 1 and 2, the flow-terminating interface 118 is a hydrophilic/hydrophobic interface. The hydrophilic/hydrophobic interface 118 is placed downstream of the sensor area 110 but is placed as close to the sensor area 110 as possible to reduce the volume of sample required. The hydrophilic/hydrophobic interface 118 terminates the flow of the sample, with the result that additional sample will not flow into the sensor area 110 if introduced at the sample application zone 120, so that analysis of the sample can be carried out on a quiescent (dormant) sample, thereby allowing consistent analyses. Sensor response is compromised if the sample flows during the analysis; thus, termination of the flow of the sample is extremely desirable. At least one opening 122 is formed in the sensor strip 100 in communication with the flow channel 114 to bleed air to reduce the pressure that resists uptake of the sample. This pressure prevents the sample from traversing the flow channel 114. In FIGS. 3 and 4 the flow-terminating interface 118a comprises a plurality of openings 122a. These openings 122a are of sufficient size and are located at sufficiently close intervals such that the capillary attraction is disrupted, whereby the force that allows the liquid to flow in the flow channel 114 is resisted.

The base layer 102 is preferably made of an inert polymeric material. Representative materials that can be used to form the base layer 102 include, but are not limited to, poly(vinyl chloride), polycarbonate, and polyester. The dimensions of the base layer 102 are not critical, but a typical base layer 102 has a length of from about 20 mm to about 40 mm, a width of from about 3 mm to about 10 mm, and a thickness of from about 0.5 mm to about 1 mm.

The conductive tracks 104a, 104b, and 104c are made of an electrically conductive material. Representative materials that can be used to form the electrically conductive tracks 104a, 104b, and 104c include, but are not limited to, carbon, platinum, palladium, gold, and a mixture of silver and silver chloride. The tracks 104a, 104b, and 104c determine the positions of electrical contacts 123a, 123b, and 123c, respectively, and the electrodes, which will be described later. The third track can be omitted in the absence of a third electrode. The electrical contacts are insertable into an appropriate measurement device (not shown).

The reaction site 106 comprises an arrangement of electrodes, and, optionally, one or more layers of reagents. The electrode arrangement of the sensor strip preferably includes either two or three electrodes. In a two-electrode system (not shown), a working electrode and dual-purpose reference/counter electrode define the electrode arrangement. A third electrode (trigger electrode) can be optionally added to indicate that the reaction site 106 is filled. The trigger electrode prevents the assay from beginning until an adequate quantity of sample has filled the reaction site 106. A two-electrode system is described more completely in U.S. Pat. No. 5,509,410, incorporated herein by reference. The reference electrode can be positioned so as to act as a trigger electrode to initiate the assay sequence in the absence of the third electrode.

In a three-electrode system, which is illustrated in FIGS. 1, 2, 3, and 4, a working electrode 124, a reference electrode 126, and a counter electrode 128 define the electrode arrangement. The function of the working electrode 124 is to monitor the reaction that takes place in the reaction site 106, e.g., the reaction of glucose with glucose oxidase or glucose dehydrogenase. The function of the reference electrode 126 is to maintain a desired potential at the working electrode. The function of the counter electrode 128 is to provide the necessary current flow at the working electrode 124. In this system the counter electrode 128 can have the secondary function of a trigger electrode, that is, prevents the assay from beginning until an adequate quantity of sample has filled the reaction site 106.

The reaction that takes place at the working electrode 124 is the reaction that is required to be monitored and controlled, e.g., the reaction of glucose with glucose oxidase or with glucose dehydrogenase. The functions of the reference electrode 126 and the counter electrode 128 are to ensure that the working electrode 124 actually experiences the desired conditions, i.e. the correct potential. The potential difference between the working electrode 124 and the reference electrode 126 is assumed to be the same as the desired potential at the working electrode 124. In an ideal reference electrode, no current passes through the reference electrode, and the reference electrode maintains a steady potential; in the case of a dual-purpose reference/counter electrode, current does pass through the dual-purpose reference/counter electrode, and thus, the dual-purpose reference/counter electrode does not maintain a steady potential. At low currents, the potential shift is small enough such that the response at the working electrode is not significantly affected, and hence the dual-purpose reference/counter electrode is designated a pseudo-reference electrode. The dual-purpose reference/counter electrode still carries out its counter electrode function; however, in the case of the dual-purpose reference/counter electrode, the potential that is applied between the dual-purpose reference/counter electrode and the working electrode cannot be altered to compensate for changes in potential at the working electrode.

The electrodes 124, 126, and 128 are made of an electrically conductive material. Representative materials that can be used to form the electrodes 124, 126, and 128 include, but are not limited to, carbon, platinum, palladium, and gold. The reference electrode 126 can optionally contain a layer comprising a mixture of silver and silver chloride. The dimensions of the electrodes 124, 126, and 128 are not critical, but a typical working electrode has an area of from about 0.5 $mm^2$ to about 5 $mm^2$, a typical reference electrode has an area of from about 0.2 $mm^2$ to about 2 $mm^2$, and a typical counter electrode has an area of from about 0.2 $mm^2$ to about 2 $mm^2$.

The working electrode 124 comprises a layer of conductive material containing a working area. The working area can include an ink (referred to a working ink), which is deposited on the layer of conductive material of the working area. The working ink comprises a reagent system that is sensitive to the analyte of interest.

The working area is formed from a working ink that includes a reagent suitable for the subject test. The reagent may include a mixture of an enzyme (e.g., glucose dehydrogenase or glucose oxidase for a glucose assay), a redox mediator (such as an organic compound, e.g., a phenanthroline quinone, an organometallic compound, e.g., ferrocene or a ferrocene derivative, a coordination complex, e.g., ferricyanide), and a conductive filler material (e.g., carbon) or non-conductive filler material (e.g., silica). Alternatively, instead of an enzyme, the working area can contain a substrate that is catalytically reactive with an enzyme to be measured. The respective printing inks are applied to the electrode 124, and, optionally, electrode 126 or electrode 128, or both, as discrete areas of fixed length. The printing inks can applied by means of screen-printing. The printing inks can further include a polysaccharide (e.g., a guar gum, an alginate, cellulose or a cellulosic derivative, e.g., hydroxyethyl cellulose), a hydrolyzed gelatin, an enzyme stabilizer (e.g., glutamate or trehalose), a film-forming polymer (e.g., a polyvinyl alcohol), a conductive filler (e.g., carbon) or non-conductive filler (e.g., silica), a defoaming agent, a buffer, or a combination of the foregoing.

The electrodes cannot be spaced so far apart that the working electrode 124, the reference electrode 126, and the counter electrode 128 (or the dual-purpose reference/counter electrode and the working electrode in an alternative embodiment) cannot be covered by the sample. It is preferred that the length of the path to be traversed by the sample (i.e., the sample path) be kept as short as possible in order to minimize the volume of sample required. The maximum length of the sample path can be as great as the length of the sensor strip. However, the corresponding increase in resistance of the sample limits the length of the sample path to a distance that allows the necessary response current to be generated. The solution resistance is also influenced by the distance from the edge of the area of the reference electrode 126 to the edge of the working area of the working electrode 124 (or by the distance from the dual-purpose reference/counter electrode to the edge of the working area of the working electrode in an alternative embodiment). Reducing the distance between the reference electrode 126 and the working electrode 124 (or the dual-purpose reference/counter electrode from the working electrode in an alternative embodiment) decreases the solution resistance. Positioning the electrodes in a spaced-apart manner has the advantage of preventing completion of a circuit (and thus preventing detection of a response current) before the working electrode has been completely covered by sample.

The elongated portions of the conductive tracks 104*a*, 104*b*, and 104*c* can optionally be overlaid with a track of conductive material, preferably made of a mixture comprising silver particles and silver chloride particles. This optional overlying track results in lower resistance, and consequently, higher conductivity. Optionally, a layer of a hydrophobic electrically insulating material 108 further overlies the tracks 104*a*, 104*b*, and 104*c*. The layer of hydrophobic electrically insulating material 108 does not cover the positions of the reference electrode 126, the working electrode 124, the counter electrode 128, and the electrical contacts. In the embodiment employing the dual-purpose reference/counter electrode (in an alternative embodiment), the layer of hydrophobic electrically insulating material does not cover the positions of the dual-purpose reference/counter electrode, the working electrode, any third electrode, and the electrical contacts. This layer of hydrophobic electrically insulating material 108 serves to prevent short circuits. Because this insulating material is hydrophobic, it can cause the sample to be restricted to the exposed electrodes. A preferred insulating material is commercially available as "POLYPLAST" (Sericol Ltd., Broadstairs, Kent, UK).

The reaction site 106 is not limited to reaction sites appropriate to electrochemical sensors. In a photometric sensor (not shown), the reaction site can comprise a reagent system that changes its optical properties (e.g., absorbance, reflectance) as a function of the presence of or the amount of an analyte. A photometric sensor is similar to the sensor shown in FIGS. 1, 2, 3, and 4, with the exception that the electrodes and tracks are removed, and, at the reaction site, at least a portion of the flow channel comprises a light transmissive material so that a source of light can transmit light through the light transmissive material to provide a signal related to the presence or the amount of an analyte in the sample, e.g., absorbance or reflectance. This optical signal can be detected and measured. In conjunction with the light transmissive material, at least one reagent for a specified assay can be located at or transported to the reaction site. In still another type of sensor (not shown), the reaction site can comprise an ion-selective electrode.

The spacer layer 112 comprises a material of substantially uniform thickness that can bond to the first major surface 130 of the base layer 102 and to the first major surface 132 of the cover layer 116. The spacer layer 112 can comprise a backing having adhesive material coated on both major surfaces thereof. Examples of backings and adhesives suitable for forming the spacer layer 112 can be found in *Encyclopedia of Polymer Science and Engineering*, Volume 13, John Wiley & Sons (1988), pages 345–368, incorporated herein by reference. Alternatively, the spacer layer 112 can be formed by printing an adhesive. Adhesives that are suitable for preparing the spacer layer 112 should be sufficiently resistant to external pressure so that the depth of the spacer layer 112 is maintained upon exposure of the sensor strip 100 to external stress.

The spacer layer 112 can be prepared in any of several ways. In one embodiment, the spacer layer can be prepared from a double-sided adhesive tape, i.e., a backing layer having a layer of adhesive on both major surfaces thereof. In another embodiment, the spacer layer 112 can be formed from an adhesive that is coated onto the base layer 102 from an aqueous carrier or from an organic carrier. In still another embodiment, the spacer layer 112 can be formed from a radiation curable adhesive, preferably ultra-violet radiation curable adhesive, the adhesive being capable of being coated onto the base layer 102. The dimensions of the spacer layer 112 are not critical, but the spacer layer 112 typically has a length ranging from about 3 mm to about 30 mm and a thickness ranging from about 50 µm to about 200 µm. The spacer layer 112 forms the sidewalls of the flow channel 114. A typical width of a flow channel 114 ranges from about 2 mm to about 5 mm.

The spacer layer 112 must be adhered to both the base layer 102 and the cover layer 116 to maintain the sensor strip 100 as an integrated unit. It is preferred that the spacer layer 112 be bonded to the cover layer 116 and the base layer 102 by means of adhesive. Preferred embodiments of the spacer layer 112 include a backing having a layer of adhesive on both major surfaces thereof. The adhesive can be a water-borne adhesive, a solvent-borne adhesive, or a radiation-curable adhesive, preferably an ultra-violet radiation curable adhesive (hereinafter "UV-curable adhesive"). Water-borne adhesives, solvent-borne adhesives, and UV-curable adhesives are preferably screen-printed so that a required design of the spacer layer 112 is printed on the base layer 102. The required design is preferably prepared from a UV-curable adhesive, because the thickness of the spacer layer that will result from curing the uncured layer of UV-curable adhesive corresponds closely to the thickness of the uncured layer of UV-curable adhesive, thereby ensuring the manufacture of a flow channel 114 having a precisely defined depth.

Commercially available products comprising backings having layers of adhesive on both major surfaces thereof include materials such as TESA 4972 (TESA Tape, Inc., Charlotte, N.C.). Such products are preferably precut before being applied to the base layer 102. U.S. Pat. No. 6,207,000 discloses a process for which a spacer layer (double-sided adhesive) is laminated onto a carrier layer and subsequently a contour that determines the shape of the channel is removed from the spacer layer.

Representative examples of water-borne adhesives suitable for use in this invention include materials such as acrylic-based KiwoPrint D-series adhesives (Kiwo, Inc., Seabrook, Tex.). One benefit of water-borne adhesives is that the humidity of the printing environment can be maintained at a desired level to avoid premature drying of the adhesive. One disadvantage of water-borne adhesives is that the depth of the flow channel 114 is reduced significantly when the aqueous carrier evaporates. In addition, water-borne adhesives may not have sufficient mechanical strength to prevent deformation when subjected to externally applied pressure.

Representative examples of solvent-borne adhesives suitable for use in this invention include materials such as acrylic-based KiwoPrint L-series and TC-series adhesives (Kiwo, Inc., Seabrook, Tex.). Solvent-borne adhesives are more difficult to use than are water-borne adhesives, because evaporation of solvent is more facile than water. In addition, the depth of the flow channel 114 decreases significantly following removal of solvent.

Representative examples of UV-curable adhesives suitable for use in this invention include materials such as Kiwo UV3295VP (Kiwo, Inc., Seabrook, Tex.), which comprises acrylic acid, benzophenone, isobornyl acrylate, isobornyl methacrylate, proprietary photoinitiator, and proprietary acrylic oligimer and polyesters. Advantages of UV-curable adhesives include resistance to drying under ambient conditions (i.e., external ultraviolet radiation is required to initiate polymerization) and the ability to maintain the thickness of layer immediately following printing throughout the curing process. As mentioned previously, the depth of the flow channel 114 derived from thickness of water-borne and solvent-borne adhesives decreases upon curing (reduction in the depth of the flow channel 114 ranges from about 40% to about 70%). The viscosity of the UV-curable adhesive can be modified from the original formulation by the inclusion of fumed silica (Cab-O-Sil M5, Cabot Corporation, Boston, Mass.). The addition of fumed silica (preferably up to 3% by weight) allows viscosity modification without adversely affecting the bonding characteristics of the cured adhesive. The increased viscosity of the ink improves the definition of the walls of the flow channel by reducing the ability of the ink to spread between the time it is printed and the time it is cured. The thickness of the spacer layer can be controlled by selecting appropriate mesh counts and thread thickness of the screen used for printing these adhesives. Alternatively, the adhesive can be screen printed by means of a stencil screen of desired thickness.

Registration tolerances of a spacer layer 112 applied by a method of printing are well suited for rapid manufacturing of a sensor having the form of a strip. In particular, the material for forming the spacer layer 112 can simply be printed at a conveniently located printing station. If the spacer layer 112 is applied by means of a tape cut from a sheet, it is required that the tape cut from the sheet be placed in the prescribed area of the sensor, so that the adhesive does not cover any area that must remain exposed. Likewise, if the spacer layer 112 is applied by means of printing of an adhesive, it is required that the adhesive be printed in the prescribed area of the sensor, so that the adhesive does not cover any area that must remain exposed.

The cover layer 116 is preferably made from an inert polymeric material. The portion of the cover layer 116 that forms a surface of the flow channel 114 is preferably hydrophilic or rendered hydrophilic by a hydrophilic coating material. This type of material for the cover layer or coating material for the cover layer is suitable for use with a sample containing a hydrophilic liquid. Representative examples of materials that can be used to form the cover layer 116 include, but are not limited to, polyester, e.g., poly(ethylene terephthalate), having a hydrophilic coating, polyester, e.g., poly(ethylene terephthalate), subjected to corona-treatment or surfactant-treatment, and poly(vinyl chloride) subjected to corona-treatment or surfactant-treatment. The dimensions of the cover layer 116 are not critical, but a typical cover layer 116 has a length of from about 15 mm to about 35 mm, a width of from about 3 mm to about 10 mm, and a thickness of from about 0.05 mm to about 1 mm. When the sample contains a hydrophobic liquid, the portion of the cover layer 116 that forms a wall of the flow channel 114 is preferably hydrophobic or rendered hydrophobic by a hydrophobic coating material. Representative materials for forming a hydrophobic coating include, but are not limited to long-chain hydrocarbons and hydrophobic surfactants. These materials are well-known to those having ordinary skill in the art.

The cover layer 116 is preferably made of a polyester material (e.g., poly(ethylene terephthalate)) having a layer of hydrophilic material coated on one major surface thereof (i.e., the surface forming a wall of the flow channel 114) to promote flow of hydrophilic fluid through the flow channel 114. Representative examples of materials suitable for preparing the cover layer 116 include 3M 9971 Hydrophilic PET film and Mitsubishi 4FOG, both of which are formed from poly(ethylene terephthalate). The layer of hydrophilic material allows the sample to wet the surface of the cover layer 116, whereby flow of the sample through the flow channel 114 is facilitated. Flow of the sample continues until the sample is removed from the flow channel 114 or the flow channel 114 consumes the entire sample. The flow-terminating interface, e.g., hydrophilic/hydrophobic interface 118, the interface 118a, causes the flow of the sample to terminate, even when additional sample is present at the inlet (sample application zone 120) of the flow channel 114.

The layer of hydrophilic material coated on the cover layer 116 assists uptake of hydrophilic fluid in the absence of external force. In other words, the sample need not be forced to fill the cavity by, for example, syringe injection. In the absence of the layer of hydrophilic material coated on the cover layer 116, a sample of hydrophilic fluid will either not fill the flow channel 114 or will require an excessive amount of time to fill the flow channel 114. If the hydrophilic/hydrophobic interface 118 is formed by removing a portion of the hydrophilic material from the cover layer 116 to form a groove, the cover layer 114 must have a hydrophobic layer below the layer of hydrophilic material to cause the groove formed therein to terminate the flow of the hydrophilic sample. If the groove is insufficiently deep, such that the ablated portion of the cover layer 116 is not hydrophobic, then the hydrophilic sample will first fill the flow channel 114 to the groove, but the groove will not be a hydrophilic/hydrophobic interface, with the result that the groove will not terminate the flow of the hydrophilic sample. Furthermore, if the hydrophilic/hydrophobic interface 118 is formed by removing a portion of the hydrophilic layer from the cover layer 116 to form a groove, the groove must be of sufficient width to prevent the sample from traversing the width of the groove merely by the momentum attributable to the flow of the sample. Capillary attraction provides momentum to the flowing sample. This momentum can cause the sample to flow at a sufficient rate of flow to allow the sample to jump over the hydrophilic/hydrophobic interface 118 located at the groove. In another situation, the solid materials in a sample of blood can span the width of the groove and create a bridge, which the sample can traverse, thereby allowing the sample to flow beyond the hydrophilic/hydrophobic interface 118. A groove having a width of about 50 $\mu$m and a depth of about 5 $\mu$m is sufficient to ensure that the flow of fluid will be terminated when the cover layer is a hydrophobic material containing a hydrophilic layer having a thickness of about 0.1 $\mu$m coated on the surface thereof. However, the depth of the groove need only be sufficient to eliminate the hydrophilic material, and the width of the groove need only be sufficient to prevent any portion of the fluid from spanning it. The precise dimensions of the groove can be determined by a trial-and-error procedure. The length of the groove is, of course, equal to or greater than the width of the flow channel 114.

The foregoing refers to a hydrophilic liquid sample flowing by means of capillary attraction along a hydrophilic cover layer. The same reasoning applies to a hydrophobic liquid sample flowing by means of capillary attraction along a hydrophobic cover layer, the only exception being that the hydrophobic layer is replaced by a hydrophilic layer and a hydrophilic coating is replaced by a hydrophobic coating.

FIGS. 5, 6, 7, 8, and 9 illustrate in greater detail various types of flow-terminating interfaces. However, it should be noted that these illustrations provide only a limited number of representative examples. There are numerous ways to provide a flow-terminating interface other than by what is shown in FIGS. 5, 6, 7, 8, and 9. In FIGS. 5, 6, 7, 8, and 9, the upstream end of the cover layer 116 is denoted by the letter "U" and the downstream end of the cover layer 116 is denoted by the letter "D".

Figure 5:
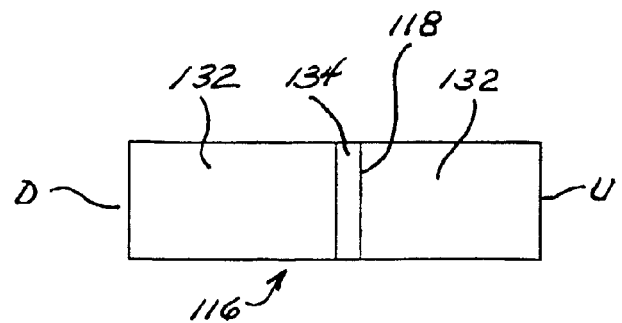
FIG. 5 is a top plan view of one embodiment of the major surface of the cover layer that forms a wall of the flow channel.

In one embodiment, as shown in FIG. 5, the hydrophilic/hydrophobic interface 118 can be made by applying to a portion of the first major surface 132 of the cover layer 116 a layer 134 of material that changes the hydrophilicity of that portion of the cover layer 116. If the first major surface 132 of the cover layer 116 is hydrophilic, the layer 134 of material to be applied to form the hydrophilic/hydrophobic interface 118 should be hydrophobic. If the first major surface 132 of the cover layer 116 is hydrophobic, the layer 134 of material to be applied to form the hydrophilic/hydrophobic interface 118 should be hydrophilic.

Figure 6:
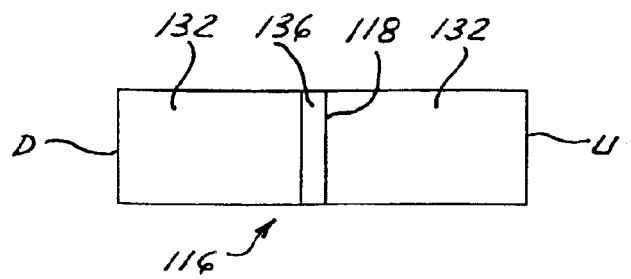
FIG. 6 is a top plan view of another embodiment of the major surface of the cover layer that forms a wall of the flow channel.

In another embodiment, as shown in FIG. 6, the hydrophilic/hydrophobic interface 118 can be made by altering the hydrophilicity of a portion 136 of the first major surface 132 of the cover layer 116 by removing a coating material from that portion 136 of the first major surface 132 of the cover layer 116. For example, if the cover layer 116 is made of a hydrophobic material and the first major surface 132 of the cover layer 116 is coated with a layer of hydrophilic material, a portion 136 of the hydrophilic material can be removed to form the hydrophilic/hydrophobic interface 118. If the cover layer 116 is made of a hydrophilic material and the first major surface 132 of the cover layer 116 is coated with a layer of hydrophobic material, a portion 136 of the hydrophobic material can be removed to form the hydrophilic/hydrophobic interface 118.

Figure 7:
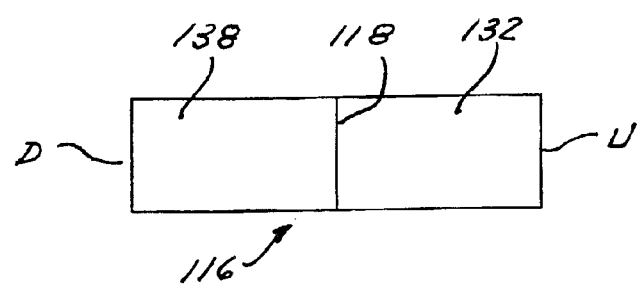
FIG. 7 is a top plan view of still another embodiment of the major surface of the cover layer that forms a wall of the flow channel.

In still another embodiment, as shown in FIG. 7, if the first major surface 132 of the cover layer 116 is made of a hydrophilic material, a portion 138 of the first major surface 132 of the cover layer 116 can be coated with a layer of hydrophobic material to form the hydrophilic/hydrophobic interface 118. If the first major surface 132 of the cover layer 116 is made of a hydrophobic material, a portion 138 of the first major surface 132 of the cover layer 116 can be coated with a layer of hydrophilic material to form the hydrophilic/hydrophobic interface 118. In all of the embodiments involving a hydrophilic/hydrophobic interface, the dimensions of the hydrophilic/hydrophobic interface are not critical, but are of sufficient magnitude to terminate the flow of a sample.

Figure 8:
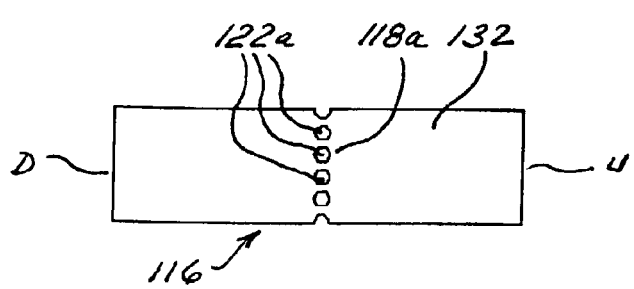
FIG. 8 is a top plan view of still another embodiment of the major surface of the cover layer that forms a wall of the flow channel.

In still another embodiment, as shown in FIG. 8, which is substantially similar to the embodiment shown in FIGS. 3 and 4, a plurality of openings 122a can be formed in the cover layer 116 in the position where the flow-terminating interface 118a is desired. These openings 122a are of sufficient size and are separated by appropriate distances to form a barrier that will disrupt the force of capillary attraction that is causing the liquid to flow in the flow channel. If the openings 122a are spaced too far apart, the flow of the fluid will not be terminated. However, it should be noted that the openings 122a should not be placed so close together that the structural integrity of the cover layer 116 is adversely affected. Likewise, the openings 122a should not be of such a size that the structural integrity of the cover layer 116 is adversely affected. The proper selection of the size of the openings 122a and the proper selection of the distance between the openings 122a can readily be determined by one of ordinary skill in the art. It is desired to employ a plurality of openings 122a so that misalignment of the cover layer 116 will not adversely affect the sensor strip.

Figure 9:
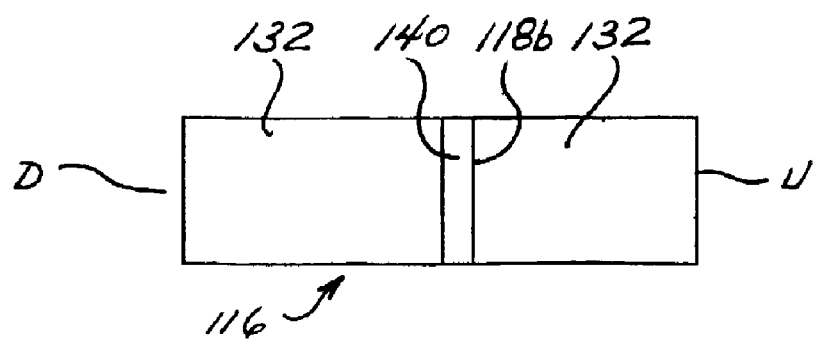
FIG. 9 is a top plan view of still another embodiment of the major surface of the cover layer that forms a wall of the flow channel.

In still another embodiment, as shown in FIG. 9, at a point in the flow channel where it is desired to place a flow-terminating interface 118b, one or more dimensions of the flow channel can be increased to such an extent that the force of capillary attraction that is causing the liquid to flow in the flow channel will be disrupted. Preferably, the depth of the flow channel is greatly increased by removing a significant amount of material from the first major surface 132 of the cover layer 116. This removal of material provides a notch-shaped flow-terminating interface 140 having a depth that is much greater than the depth of the flow channel upstream of the flow-terminating interface 118b. The mechanism of this mode of flow disruption is brought about when the force arising from the weight of the fluid exceeds the force arising from capillary attraction. Selection of the dimensions of the flow channel to bring about this effect can be carried out by trial and error. Any of the foregoing embodiments will provide a flow-terminating interface suitable for use with the flow channel described herein.

The dimensions of the flow channel 114 are set such that the sample of fluid fills the flow channel 114 by capillary attraction. If the design of the flow channel 114 is altered by means of a flow-terminating interface or by increasing the dimensions of the flow channel to reduce the effect of capillary attraction, then the forces attributable to capillary attraction that allow a sample to be taken up are insufficient to permit additional fluid to enter the flow channel.

As stated previously, in accordance with this invention, the flow channel 114 is designed so that liquid samples flow along those major surfaces or portions of major surfaces of the flow channel 114 that contain the flow-terminating interface. The flow channel 114 is designed so that liquid samples do not flow along those major surfaces or portions of those major surfaces of the flow channel that do not contain a flow-terminating interface. This design is necessary so that the liquid sample will cease to flow when it encounters the flow-terminating interface.

An opening is required in the sensor strip to allow air to flow out of the flow channel 114. The opening can be placed in the base layer 102, the cover layer 116, or the spacer layer 112. In the preferred embodiment, at least one opening 122 in the spacer layer 112 downstream of the flow-terminating interface 118 allows the air in the flow channel 114 to vent as the sample is being introduced into the flow channel 114.

The sensor strip 100 can have one or more openings 122 in the spacer layer 112 and communicating with the flow channel 114. See FIGS. 1 and 2. If there are no openings in the cover layer 116 or in the base layer 102, the positioning of the openings 122 is determined by the registration of the base layer 102, the spacer layer 112, and the cover layer 116.

In an alternative embodiment, the cover layer 116 can have a plurality of openings 122a in the vicinity of the flow channel 114 to allow gases in the flow channel 114 to be removed upon the addition of the sample of fluid. See FIGS. 3 and 4. The plurality of openings 122a allows reduction of the registration tolerance as compared to a system with a single opening in the cover layer 116. In otherwords, the openings 122a can be spaced apart in order to maintain the structural integrity of the sensor strip 100, with the result that some of the openings 122a may be positioned in such a way that they will not communicate with the flow channel 114, thereby preventing their ability to function as a vent. However, the formation of a plurality of openings 122a will result in providing venting and structural integrity of the sensor strip 100 substantially equivalent to the embodiment in which the openings 122 are formed in the spacer layer 112. This embodiment differs from the embodiment described previously in that a plurality of openings 122a are included in the cover layer 116 rather than a single opening in the cover layer 116 or in the spacer layer 112. If desired, the openings can serve to act as a flow-terminating interface, so long as the opening are of sufficient size and are separated from one another by appropriate distances.

The sensor strip 100 described herein can be used as a test strip for monitoring blood glucose level. The sensor strip 100 described herein does not employ a layer of mesh to improve flow of sample to the electrodes. The deletion of the layer of mesh reduces the time of manufacturing and the cost of manufacturing. In addition, the volume of sample required is reduced by removal of the layer of mesh.

This invention provides an unlimited number of designs of the flow channel, for which a single cover layer including a flow-terminating interface can be used. Precise registration of openings formed in the cover layer with the flow channel is not required. The design of the flow channel of this invention also allows for adequate adhesion between the base layer and the cover layer. More importantly, a sensor strip is provided in which dilution of a reagent can be minimized and a quiescent sample state following uptake of the sample into the flow channel can be maintained, which results in consistent analyses of analytes.

The following non-limiting examples further illustrate this invention.

EXAMPLES

Example 1

This example illustrates the preparation of a sensor strip according to this invention. The sensor strip of this example is shown in FIGS. 1 and 2.

Carbon tracks are applied to a base layer made of poly (vinyl chloride) (PVC) by means of a screen-printing technique. The carbon tracks define the position of the electrodes within the reaction site, which includes the reference electrode, counter/trigger electrode, and working electrode. The counter electrode also functions as a trigger electrode. The assay begins when the sample contacts the trigger electrode. The carbon tracks also define the position of the contacts. An insulation layer can be printed over carbon tracks to expose the defined reaction site. The insulation layer is characterized by having a portion cut therefrom to create electrical contacts that can be inserted into a meter for measuring the reaction of interest. UV-curable adhesive can be printed to form the spacer layer and define the sidewalls of the flow channel. UV-curable adhesive is preferred to water-borne or solventborne adhesives, because the thickness of the cured layer is similar to the thickness of the uncured layer as applied. The cover layer comprises a layer of surfactant-treated polyester (3M 9971 Hydrophilic PET film). A low intensity laser beam can be used to create a hydrophilic/hydrophobic interface in the cover layer, by ablating a single region having a width of 50 $\mu$m and a depth of 5 $\mu$m to remove the hydrophilic coating such that the hydrophobic layer is exposed to the sample in the flow channel; however, more than one region can be ablated to reduce the possibility of the sample traversing the single ablated region and flowing beyond the desired point of flow termination. Additional ablated regions spaced less than 2 mm apart are sufficient for this purpose. The thus ablated cover layer will allow samples comprising a hydrophilic liquid to be taken up into the flow channel. The cover layer is placed on the spacer layer such that the hydrophilic/hydrophobic interface is upstream of the openings that constitute the vents and downstream of the reaction site.

In order for the sensor strip to be used, the sample enters the flow channel at the sample application zone and is caused to traverse the flow channel by capillary attraction, resulting from the hydrophilic nature of the coating on the cover layer. Flow of the sample is terminated when the sample reaches the hydrophilic/hydrophobic interface. Flow of the sample terminates even if additional sample is present at the sample application zone.

The proximal end of the sensor strip can optionally be trimmed to produce a sample application zone in which the sample is taken up at the proximal end of the strip. This type of sensor strip is commonly referred to as an end-fill sensor strip. The invention is not limited to fabrication of a single end-fill sensor strip. A plurality of end-fill sensor strips can be fabricated at the same time. Following the fabrication of a plurality of end-fill sensor strips on a sheet, the sensor strips can be separated to create a plurality of individual sensor strips.

Example 2

In this example, the sensor strip of Example 1 is prepared, with the exception that a mixture of silver and silver chloride is printed on the track leading from the working electrode to reduce the resistance along that portion of the track.

Example 3

In this example, the sensor strip of Example 2 is prepared, with the exception that a reagent layer is printed on the working electrode. This optional reaction layer comprises an enzyme, a mediator, an optional binder, and an optional filler.

Example 4

In this example, the sensor strip of Example 3 is prepared, with the exception that a reagent layer is applied over all three electrodes.

Example 5

In this example, the sensor strip of Example 4 is prepared, with the exception that a layer comprising a mixture of silver and silver chloride is printed on the counter/trigger electrode and the reference electrode. This option is desired when the reagent layer cannot provide the reference voltage desired at the reference electrode.

Example 6

In this example, the sensor strip of Example 1 is prepared, with the exception that the cover layer is replaced with a cover layer wherein a hydrophobic coating is applied over a portion of the hydrophilic surface of the cover layer to render a portion of the cover layer hydrophobic, thereby creating a hydrophilic/hydrophobic interface.

Example 7

In this example, the sensor strip of Example 1 is prepared, with the exception that the cover layer is replaced with a cover layer, wherein the proximal portion of a hydrophobic PET support is coated with a hydrophilic coating. In this embodiment, the step of coating a hydrophobic material over a hydrophilic coating is eliminated. The hydrophilic portion of the cover layer is placed at the proximal end of the sensor to allow the uptake of a hydrophilic liquid.

Example 8

In this example, the sensor strip of Example 1 is prepared, with the exception that the sensor strip employs a spacer layer that has no openings in the sidewalls thereof to serve as vents. The sensor strip employs a cover layer that comprises a plurality of openings to serve both as the flow-terminating interface and as vents. A low intensity laser is used to form the openings in the cover layer. As in Example 1, the material used to form the cover layer is 3M 9971 Hydrophilic PET film. The openings, which went through the cover layer, were 0.4 mm diameter and spaced apart by 1 mm, measured from the center of one opening to the center of the adjacent opening. The cover layer is placed on the spacer layer with the hydrophilic surface facing the flow channel. Uptake of a sample comprising a hydrophilic liquid is brought about by capillary attraction between the liquid and the hydrophilic coating of the cover layer. The openings act as a flow-terminating interface by reducing the capillary attraction between the sample and cover layer by sufficiently reducing the area of the hydrophilic coating of the cover layer at the openings. An opening in the spacer layer is not required, because the openings in the cover layer communicating with the flow channel not only act as a flow-terminating interface, but also act as vents. The sensor strip of this example is shown in FIGS. 3 and 4.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A sensor strip comprising:
   (a) a base layer having a first major surface and a second major surface;
   (b) a cover layer having a first major surface and a second major surface, the first major surface of said cover layer facing the first major surface of said base layer;
   (c) a spacer layer interposed between the first major surface of said cover layer and the first major surface of said base layer to separate said cover layer from said base layer;
   (d) a flow channel having walls formed by said first major surface of said cover layer, said first major surface of said base layer, and said spacer layer, said flow channel having a reaction site therein, wherein said reaction site includes an electrode arrangement, said flow channel being of such dimensions that a liquid sample can be drawn therein and can flow therethrough by means of capillary attraction;
   (e) a flow-terminating interface applied to or formed in said first major surface of said cover layer, said flow-terminating interface capable of terminating flow of a sample of liquid in said flow channel at said flow-terminating interface;
   (f) a sample application zone, where a liquid sample is introduced into said flow channel; and
   (g) at least one opening communicating with said flow channel to allow gas to be vented from said flow channel.

2. The sensor strip of claim 1, wherein said electrode arrangement comprises a working electrode and a dual-purpose reference electrode/counter electrode.

3. The sensor strip of claim 2, wherein said electrode arrangement further includes a trigger electrode.

4. The sensor strip of claim 2, wherein said electrode arrangement further includes a reagent system on at least said working electrode.

5. The sensor strip of claim 4, wherein said reagent system comprises an enzyme and a mediator for said enzyme.

6. The sensor strip of claim 1, wherein said electrode arrangement comprises a working electrode, a counter electrode, and a reference electrode.

7. The sensor strip of claim 6, wherein said electrode arrangement further includes a trigger electrode.

8. The sensor strip of claim 6, wherein said electrode arrangement further includes a reagent system on at least said working electrode.

9. The sensor strip of claim 8, wherein said reagent system comprises an enzyme and a mediator for said enzyme.

10. The sensor strip of claim 1, wherein said at least one opening is formed in said spacer layer.

11. The sensor strip of claim 1, wherein said at least one opening is formed in said cover layer.

12. The sensor strip of claim 1, wherein said spacer layer comprises a layer of adhesive.

13. The sensor strip of claim 12, wherein said adhesive is formed from a radiation-curable adhesive.

14. The sensor strip of claim 12, wherein said adhesive is formed from a water-borne adhesive or a solvent-borne adhesive.

15. The sensor strip of claim 1, wherein said spacer layer comprises a backing having a layer of adhesive on both major surfaces thereof.

16. The sensor strip of claim 1, wherein said flow-terminating interface is a hydrophilic/hydrophobic interface.

17. The sensor strip of claim 16, wherein said hydrophilic/hydrophobic interface comprises a layer of hydrophobic material having a coating of hydrophilic material thereon, a portion of said hydrophilic material being removed to expose said hydrophobic material to said liquid in said flow channel.

18. The sensor strip of claim 16, wherein said hydrophilic/hydrophobic interface comprises a layer of hydrophilic material having a coating of hydrophobic material thereon, a portion of said hydrophobic material being removed to expose said hydrophilic material to said liquid in said flow channel.

19. The sensor strip of claim 1 wherein said first major surface of said cover layer comprises a hydrophilic material having a hydrophobic coating applied to a portion thereof.

20. The sensor strip of claim 1, wherein said first major surface of said cover layer comprises a hydrophobic material having a hydrophilic coating applied to a portion thereof.

21. The sensor strip of claim 1, wherein said flow-terminating interface comprises a plurality of openings in said cover layer.

22. The sensor strip of claim 1, wherein at least one dimension of said flow channel at said flow-terminating interface is of sufficient size that the force attributable to capillary attraction is insufficient to permit additional fluid to enter said flow channel.

23. A device for allowing the flow of a liquid and for terminating the flow of said liquid, said device comprising;
   (a) a flow channel bounded by a wall, said flow channel having dimensions to allow a liquid to flow by capillary attraction; and
   (b) a flow-terminating interface to terminate the flow of said liquid in said flow channel at said flow-terminating interface, wherein said flow-terminating interface comprises a plurality of openings in said wall of said flow channel.

* * * * *